US005790251A

United States Patent [19]
Hagiwara

[11] Patent Number: 5,790,251
[45] Date of Patent: Aug. 4, 1998

[54] DEFECT INSPECTING APPARATUS

[75] Inventor: Tsuneyuki Hagiwara, Kawasaki, Japan

[73] Assignee: Nikon Corporation, Tokyo, Japan

[21] Appl. No.: 891,067

[22] Filed: Jul. 10, 1997

Related U.S. Application Data

[63] Continuation of Ser. No. 633,379, Apr. 17, 1996, abandoned.

[30] Foreign Application Priority Data

| Apr. 19, 1995 | [JP] | Japan | 7-094061 |
| Mar. 28, 1996 | [JP] | Japan | 8-073017 |

[51] Int. Cl.$^6$ ............................. G01B 9/02; G01B 2/88
[52] U.S. Cl. ............................ 356/351; 356/237
[58] Field of Search .......................... 356/237, 390, 356/394, 351, 359, 360, 239; 382/144

[56] References Cited

U.S. PATENT DOCUMENTS

| 4,468,120 | 8/1984 | Tanimoto et al. | 356/237 |
| 4,669,885 | 6/1987 | Ina | 356/239 |
| 5,563,702 | 10/1996 | Emery et al. | 356/237 |

FOREIGN PATENT DOCUMENTS 60-8705  1/1985  Japan ................................ 356/237

*Primary Examiner*—F. L. Evans
*Attorney, Agent, or Firm*—Shapiro and Shapiro

[57] ABSTRACT

A defect inspecting apparatus for detecting a defect on a mask formed with a predetermined pattern comprises a first illumination system for transmission-illuminating the mask with light beams, a second illumination system for vertically illuminating the mask with the light beams, a first light receiving optical system for receiving illumination light beams emitted from the first illumination system and penetrating the mask and for forming an image, a second light receiving optical system for receiving illumination light beams emitted from the second illumination system and reflected by the mask and for forming an image, a first photoelectric converting element for detecting the image formed by the first light receiving optical system, a second photoelectric converting element for detecting the image formed by the second light receiving optical system and a signal processing circuit for detecting the defect on the basis of signals from the first and second photoelectric converting elements.

18 Claims, 8 Drawing Sheets

FIG. 4B

DEFECT INSPECTING APPARATUS

This is a continuation of application Ser. No. 08/633,379 filed Apr. 17, 1996, now abandoned.

BACKGROUND OF THE INVENTION

1. Field of the Invention

The present invention relates generally to a defect inspecting apparatus and, more particularly, to an apparatus for optically detecting a defect on a photo mask formed with a circuit pattern of an IC, etc.

2. Related Background Art

A known prior art apparatus for detecting a defect on a photo mask is disclosed in the Publication of U.S. Pat. No. 4,468,120. Disclosed in this Publication is a defect inspecting apparatus including an irradiation optical system for irradiating the photo mask with laser beams and a plurality of detectors for receiving scattered and diffracted light beams from the photo mask. This type of apparatus detects the defect by making use of a difference in directivity between the scattered light from the defect and the scattered light from a circuit pattern. More specifically, a logical product of signals from the plurality of detectors is taken, and, when this logical value is [1], it is determined that the defect is adhered onto the mask.

The prior art defect inspecting apparatus described above detects the defect by receiving only higher-order spatial frequency components of the scattered light beams from the defect. An intensity of the scattered light of the higher-order spatial frequency components is small, and hence there is such a problem that a flat defect and a semi-transparent defect are hard to detect.

SUMMARY OF THE INVENTION

It is a primary object of the present invention, which was contrived in view of the problems inherent in the prior arts, to provide a mask defect inspecting apparatus capable of detecting a flat defect and a semi-transparent defect existing on a mask.

According to one aspect of the present invention, a defect inspecting apparatus for detecting a defect on a mask formed with a predetermined pattern comprises a first illumination system for transmission-illuminating the mask with light beams; a second illumination system for vertically illuminating the mask with the light beams; a first light receiving optical system for receiving illumination light beams emitted from the first illumination system and penetrating the mask and for forming an image; a second light receiving optical system for receiving illumination light beams emitted from the second illumination system and reflected by the mask and for forming an image; a first photoelectric converting element for detecting the image formed by the first light receiving optical system; a second photoelectric converting element for detecting the image formed by the second light receiving optical system; and a signal processing circuit for calculating a difference or a relative signals between a signal from the first photoelectric converting element and a signal from the second photoelectric converting element and detecting the defect on the basis of the difference or the relative signal therebetween.

According to the present invention, only the light transmitting defect can be detected by disappearing substantially the whole of the circuit pattern image.

BRIEF DESCRIPTION OF THE DRAWINGS

Other objects and advantages of the present invention will become apparent during the following discussion in conjunction with the accompanying drawings, in which:

FIGS. 4A to 4E are explanatory diagrams showing a relationship between the reflected image and the transmitted image;

DETAILED DESCRIPTION OF THE PREFERRED EMBODIMENTS

Figure 1:
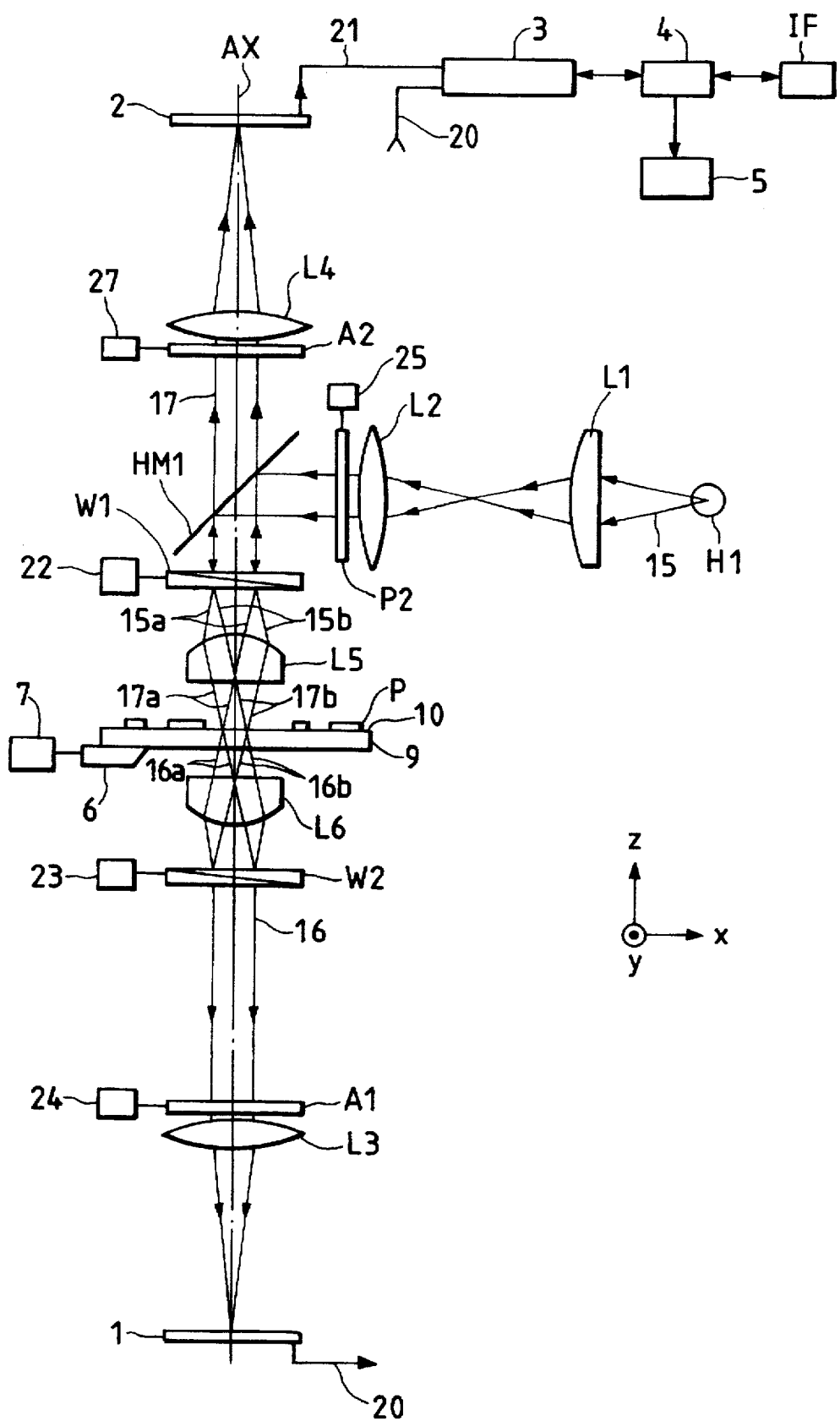
FIG. 1 is a view illustrating a defect inspecting apparatus in a first embodiment of the present invention.

FIG. 1 is a view schematically illustrating a construction of a defect inspecting apparatus suitable to a first embodiment of the present invention. Light beams 15 emitted from a light source H1 such as a mercury lamp, etc. pass through lenses L1, L2 and become rectilinear polarized light beams through a polarizer P2. The polarized light beams are then reflected downward by a half-mirror HM1. The light beams 15 reflected by the half-mirror HM1 travels forward along an optical axis AX and then fall on a Wollaston prism W1. Light beams 15a, 15b emerging from the Wollaston prism W1 are rectilinear polarized light beams having polarization planes orthogonal to each other with a lateral deviation by a predetermined quantity within a pattern plotting surface 10 for a reticle 9. The light beam 15a has a polarizing direction perpendicular to the sheet surface, while the light beam 15b has a polarizing direction parallel to the sheet surface. The reticle 9 is illuminated with the light beams 15a, 15b via the lens L5. Light beams 16a, 16b including transmission scattered light beams penetrating light transmitting areas of the reticle 9 are incident on an object lens L6 located under the reticle 9 and the fall on Wollaston prism W2. The Wollaston prism W2 synthesizes the light beams 16a, 16b into light beams 16. The light beams 16 containing the transmission scattered light beams travel through an analyzer A1 and turn out coherent light beams. The coherent light beams are image-formed on a light detection surface (light receiving surface) of a two-dimensional photoelectric converting element 1 via a lens L3.

On the other hand, rectilinear polarized light beams 17a, 17b orthogonal to each other and containing reflection scattered light beams reflected corresponding to reflectivities of a glass area and a pattern area of the reticle 9 pass through the Wollaston prism W1 and are thereby synthesized into light beams 17. The light beams 17 penetrate an analyzer A2 and become coherent light beams. The coherent light beams are refracted by a lens L4 and are image-formed on a light detection surface (light receiving surface) of a two-dimensional photoelectric converting element 2.

The polarizer P2, the analyzers A1, A2 are variable in their directions to the optical axis AX by adjusting mechanisms 25, 24, 27, respectively. The polarizer P2 and the two analyzers A1, A2 shall be in crossed Nicol relationship.

The Wollaston prisms W1, W2 are also provided with adjusting mechanisms 22, 23 capable of adjusting a relative phase difference between two fluxes of rectilinear polarized light beams orthogonal to each other but split or synthesized per polarization.

In the Wollaston prisms W1, W2, the relative phase difference between these two fluxes of rectilinear polarized light beams is zeroed by the adjustment. Further, directions of wedges are determined so that an amplitude ratio of the two fluxes of light beams to be split is 1:1. Accordingly, the polarization plane of the light beams 15 in FIG. 1 are 45° to the wedges of the two prisms W1, W2.

Note that the reticle 9 is placed on a reticle stage 6 movable in two-dimensional directions by a reticle moving unit 7.

With the above setting, when observing the reticle with no pattern, light intensities, on the light detection surfaces, of the two photoelectric converting elements 1, 2 are zeroed, and the two images, i.e., a reflection differential interference contrast image (hereinafter abbreviated to R-DIC image) and a transmission differential contrast image (hereinafter abbreviated to T-DIC image) become so-called optical dark field images. The R-DIC image and the T-DIC image are photoelectrically converted into imaging signals 21, 20.

The imaging signals 21, 20 are signals proportional to intensities and becomes single-aid (positive signal). Those signals are, after proper gain setting (hereinafter described later) has been made, inputted to a comparator 3, thereby obtaining a bipolar difference signal with + and − deflections. A window comparator circuit (a circuit within the comparator 3) having two high and low threshold values (THH, THL) extracts a defect from that difference signal. A position and a size of the thus extracted defect is outputted to a computer 4. The computer 4 controls a reticle moving unit 7 and the comparator 3 as well and outputs a result of examination to a display 5. An interface IF inputs control conditions of the apparatus from an operator.

The differential interference image of a transmission illumination is different from the reflection differential interference image of a vertical illumination when observed.

An explanation thereof will be at first given in the case of observing the circuit pattern image of the photomask through the transmission illumination.

Figure 2A:
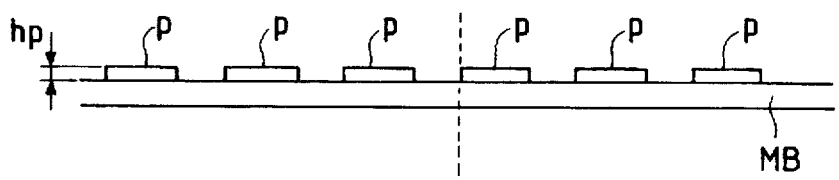
FIGS. 2A to 2C are explanatory diagrams showing a relationship between a reflected image and a transmitted image.

FIG. 2A illustrates a plotted mask blank MB of a circuit pattern p, wherein hp is a thickness of the circuit pattern p.

Figure 2B:
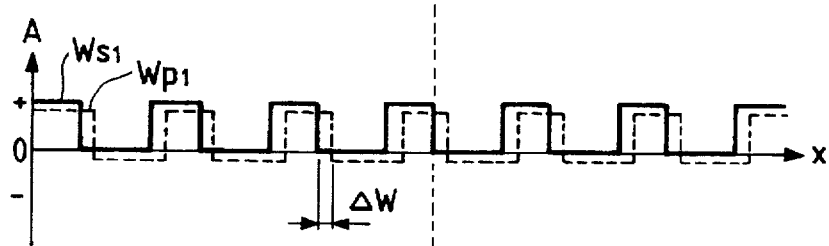

FIG. 2B shows an amplitude distribution of two light waves $W_{S1}$, $W_{P1}$ which form the transmission differential interference image conjugate to the mask blank MB on the two-dimensional photo-electrical converting element 1 through polarizing interference of the two light waves. According to a differential interference microscopic method, an X-directional lateral deviation (sheer) Δw is given to those two light waves.

The transmitting illumination light beams penetrate the glass area where the pattern p does not exist, thereby obtaining the amplitude distribution as shown in FIG. 2B.

Figure 2C:
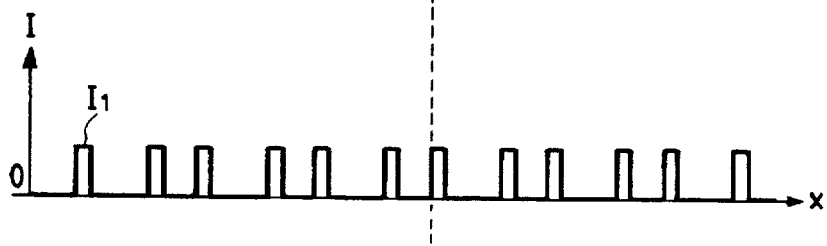

FIG. 2C shows a transmission differential interference image $I_1$ on the two-dimensional photoelectric converting element 1. Referring to FIG. 2B, an overlapped portion of $W_S$, $W_P$ is to be observed bright.

Given next is an explanation of observing the circuit pattern image of the photo mask according to a reflection differential interference method by the vertical illumination.

Figure 3A:
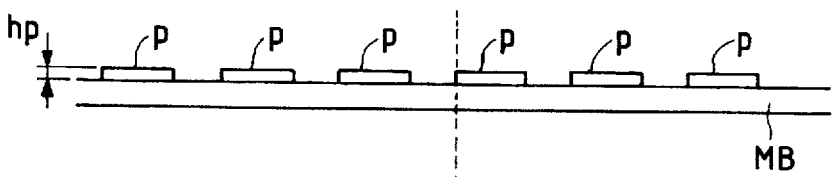
FIGS. 3A to 3C are explanatory diagrams showing a relationship between the reflected image and the transmitted image.
Figure 3B:
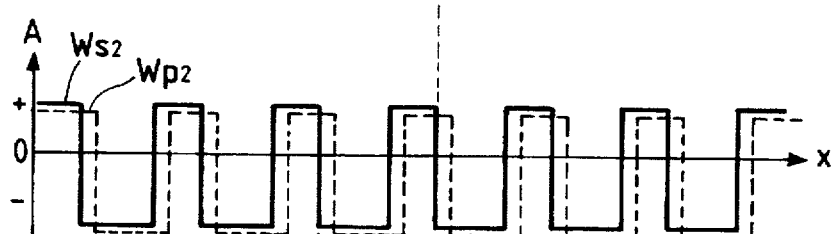

FIG. 3A illustrates the same photo mask as that in FIG. 2A. FIG. 3B shows an amplitude distribution of two light waves $W_{S2}$, $W_{P2}$ which form the reflection differential interference image conjugate to the mask blank MB on the two-dimensional photo-electrical converting element 2 through the polarizing interference of the two light waves. According to a differential interference method, the X-directional lateral deviation Δw is given to those two light waves.

The reflection illumination light beams are reflected at only amplitudes corresponding to the reflectivities of the glass area and the pattern area on the mask blank MB.

Further, the reflecting illumination light beams are, when reflected, subjected to a phase variation depending on a pattern thickness $h_P$. FIG. 3B is a diagram showing a state when receiving the phase variation by $\pi$.

Figure 3C:

FIG. 3C illustrates a reflection differential interference image I2 on the two-dimensional photoelectric converting element. Referring to FIG. 3B, an overlapped portion of $W_{S2}$, $W_{P2}$ is to be observed bright.

Note that if the phase variation due to the pattern thickness $h_P$ is not $\pi$, there is no change in the position and in the shape though a value of wave height of an intensity distribution $I_2$ varies. Hence, if gains of the photoelectric converting elements 1, 2 are adjusted in the intensity distribution $I_1$ in FIGS. 2A to 2C and the intensity distribution $I_2$ in FIGS. 3A to 3C, absolutely the same image can be obtained, and a difference image can be disappeared.

Similarly, a relative signal between the imaging signals 20, 21 is calculated, and a relative image can be disappeared based on an intensity distribution of this relative signal.

Figure 4A:
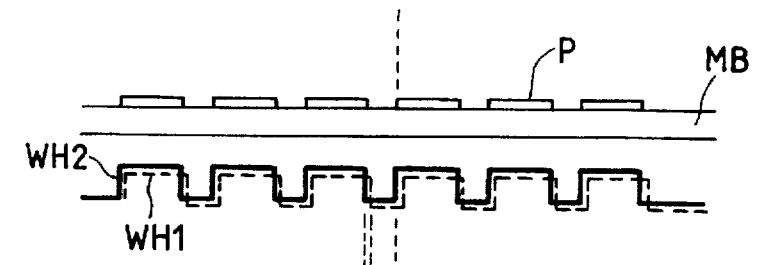
Figure 4C:
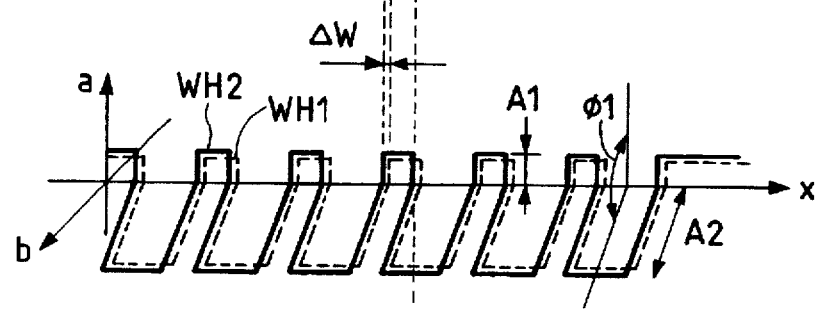
Figure 4D:
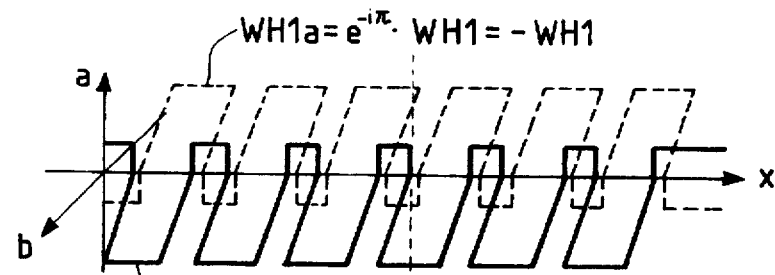

FIGS. 4A to 4E are diagrams corresponding to a case where the phase variation due to the pattern thickness $h_P$ is $\phi_1$ or a case where there is the phase difference $\phi_1$ between the glass area and the pattern as in the case of a half-tone reticle or the like. FIG. 4B illustrates two polarization planes orthogonal to each other, i.e., wave fronts WH1, WH2 of two light waves having a lateral deviation Δw. FIG. 4C is a diagram when those amplitude distributions are expressed in vector. According to the present invention, there is obtained such an optical dark field image that the image intensity is zeroed in an area exhibiting a phase difference of zero and an amplitude ratio of 1 according to the polarizing interference method. Accordingly, referring to FIG. 4C, the area with the phase difference zero and the amplitude ratio of 1 is erased. Referring to FIG. 4D, a light wave WH1' is obtained by multiplying the one light wave WH1 by a phase difference which follows:

Phase Difference $e^{-i\pi}$ (where e is the natural number, and i is the complex number.)

Figure 4E:
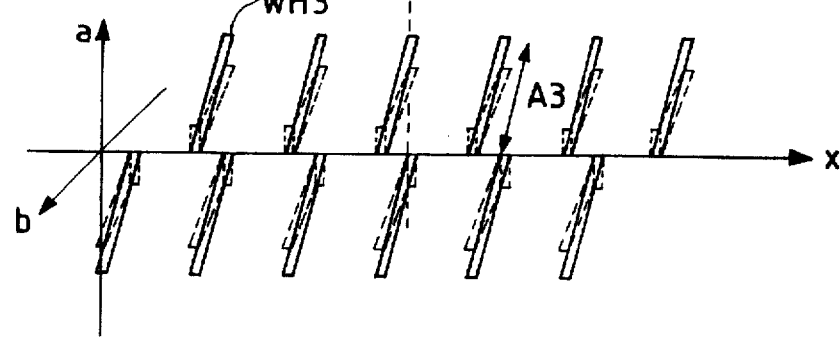
Figure 5:
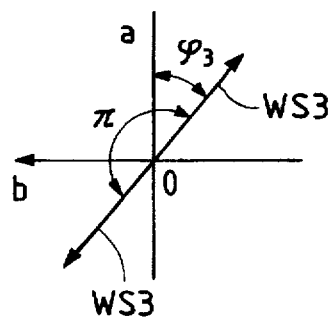
FIG. 5 is an explanatory diagram showing a relationship between a reflected image and a transmitted image.

As obvious from the diagram, in the synthetic amplitude WH3=WH1'+WH2, as shown in FIGS. 4E and 5, a real function is inclined by $\phi_2$ to the X-axis. Generally, according to the present invention, if a residual amplitude becomes a function obtained by multiplying the real function by a phase constant that does not depend on the position when the two light waves representing, as described above, the circuit pattern to be erased are optically converted into the dark field by the polarizing interference, the circuit pattern image can be erased by taking a difference between the two images, i.e., the R-DIC image and the T-DIC image.

Figure 6:
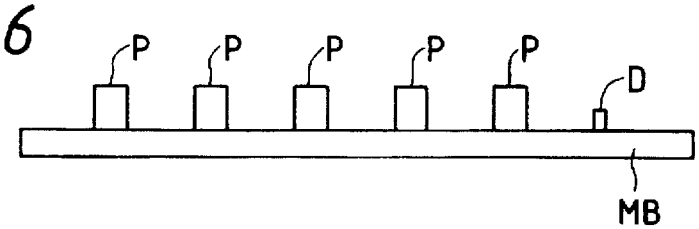
FIG. 6 is an explanatory diagram showing a relationship between the reflected image and the transmitted image.
Figure 7A:
FIGS. 7A to 7C are explanatory diagrams showing a relationship between the reflected image and the transmitted image.
Figure 7B:
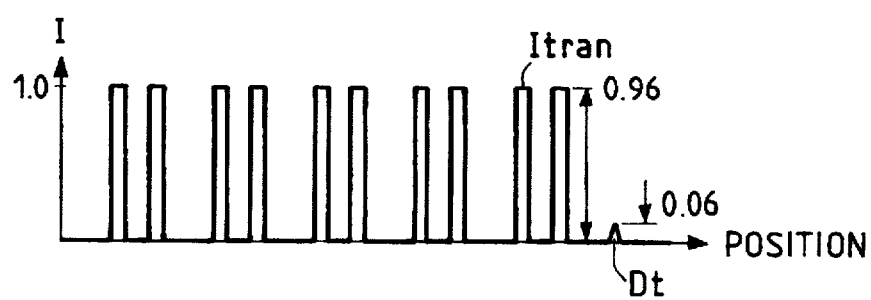
Figure 7C:
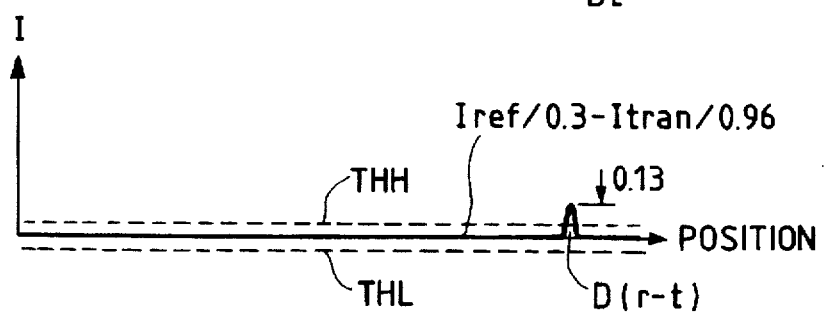

Next, as shown in FIG. 6, it is considered that there exist the pattern P and a defect D on the mask blank MB. FIG. 7A shows an intensity distribution (I) of the R-DIC image. Further, normally a reflectivity of chrome is 30%. The intensity distribution is standardized by the reflectivity and plotted, wherein there is shown 1 at a reflectivity of 100%. The defect D is a dielectric substance and is smaller than the sheer quantity Δw, and the R-DIC image thereof is relatively low because of a wave height value being approximately 0.06 when considering the one assuming the same phase with the pattern at a reflectivity of 10%. This is because a plane wave component is lost by the interference. FIG. 7B similarly illustrates the T-DIC image standardized by a transmissivity, wherein an image-of-defect Dt has a wave height value of about 0.06. FIG. 7C illustrates a difference image, wherein Iref/0.3−Itran/0.96 is set so that the values of the R-DIC image and the T-DIC image are zeroed in terms of the wave height value of the pattern image. In this case, the image-of-defect takes a positive value on the order of 0.13. If the defect is larger than the sheer quantity Δw, however, the T-DIC image is remarkably brighter than the R-DIC image, depending on a difference between light paths, and Iref/0.3−Itran/0.96<0 will be set as the case may be. It is therefore required that the window comparator circuit should detect the defect, wherein a comparator level is given based on the two threshold values THH, THL. Further, even if the defect is smaller than the sheer quantity Δw, and if the pattern and the phase are different, a high contrast (high image intensity) is to be obtained in the R-DIC or T-DIC image, whereby a minute phase substance can be detected. Moreover, the light path difference is not the same between the R-DIC image of the phase object defect and the T-DIC image of the phase object defect, and hence the image intensity differs. There is almost no possibility in which the difference image therebetween is zeroed after compensating the gain.

Similarly, there is almost no possibility in which the relative image between the R-DIC image of the phase object defect and the T-DIC image of the phase object defect becomes 1.

Figure 8:
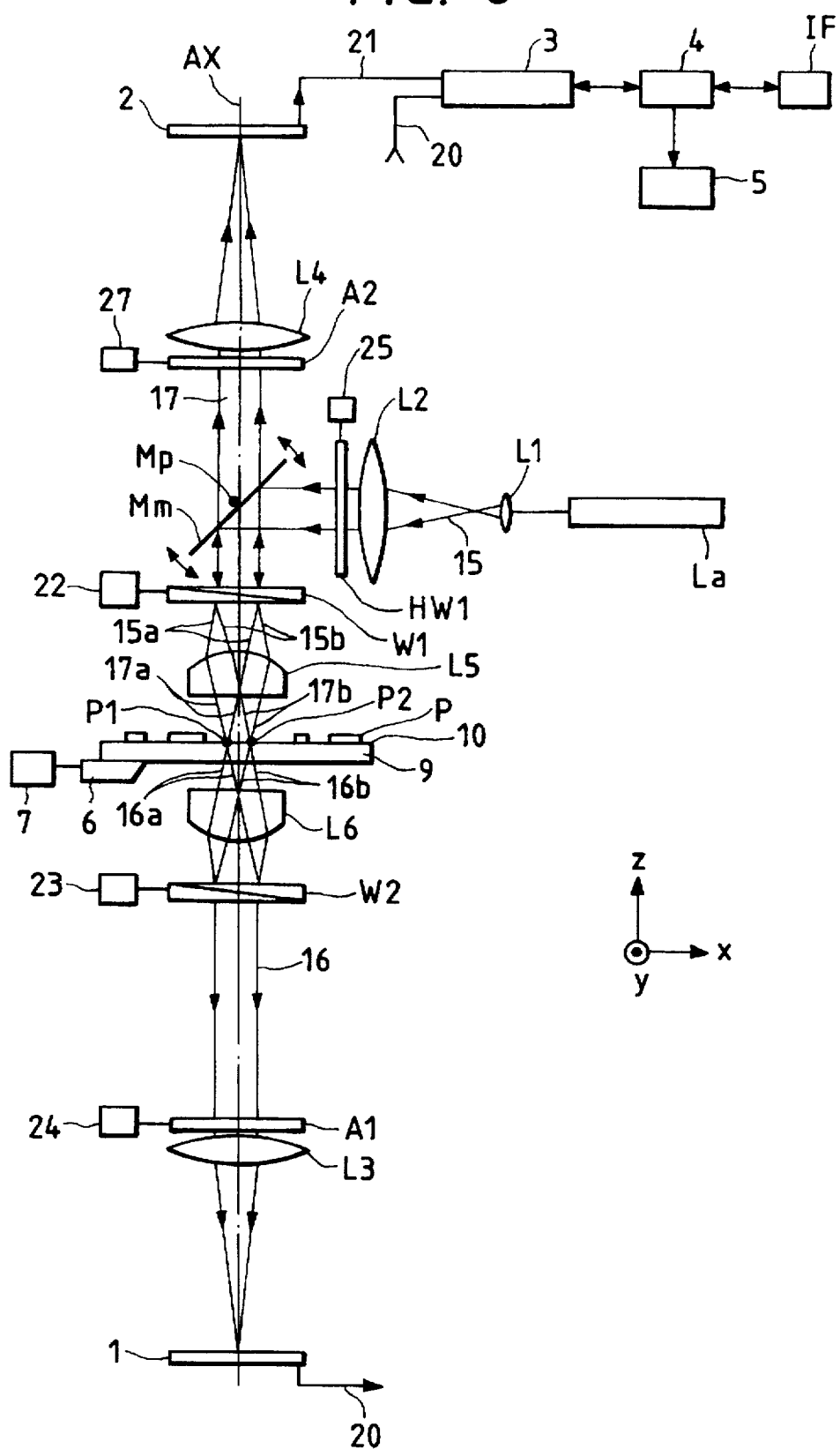
FIG. 8 is an explanatory view illustrating a second embodiment of the present invention.

FIG. 8 schematically illustrates a defect inspecting apparatus suitable for a second embodiment of the present invention. The same members as those in FIG. 1 are marked with the like symbols, and the detailed explanation will be omitted.

In accordance with the first embodiment, the interior of the field is illuminated en bloc with the light beams. In accordance with the second embodiment, however, an oscillation mirror Mm is rotated about a rotary shaft (perpendicular to the sheet surface) by use of a driving system MP. With rotations of this oscillation mirror Mm, the reticle 9 is scanned by the light beams 15. For this purpose, in accordance with the second embodiment, the light source involves the use of a laser La capable of obtaining a high luminance. The oscillation mirror Mm is a half-mirror which transmits light beams 17a, 17b emerging from the reticle 9. Accordingly, as in the first embodiment, the light beams reach the photoelectric converting element 2. The light beams emitted from the laser La are adjustable in terms of angles of the polarization planes by use of a λ/2 wavelength plate HW1. The polarization planes of the light beams 15 are directed at 45° to the directions of wedges of the Wollaston prisms W1, W2 and in the cross Nicol relationship with respect to the analyzers A1, A2. The light beams 15 form two spots P1, P2 of the rectilinear polarized light beams orthogonal to each other on a surface (pattern surface) 10 of the reticle 9 with the aid of the Wollaston prism W1 and a lens L5. An interval therebetween is a sheer quantity and kept in a fixed value, and the surface 10 is thus scanned by the light beams 15a, 15b.

In accordance with the second embodiment, the photoelectric converting elements 1, 2 in use are of a one-dimensional type and move at an equal velocity in a y-direction while synchronizing with the beam scan (synchronizing with a movement of the half-mirror Mm), thus making it possible to inspect a two-dimensional area on the reticle 9.

Figure 9:
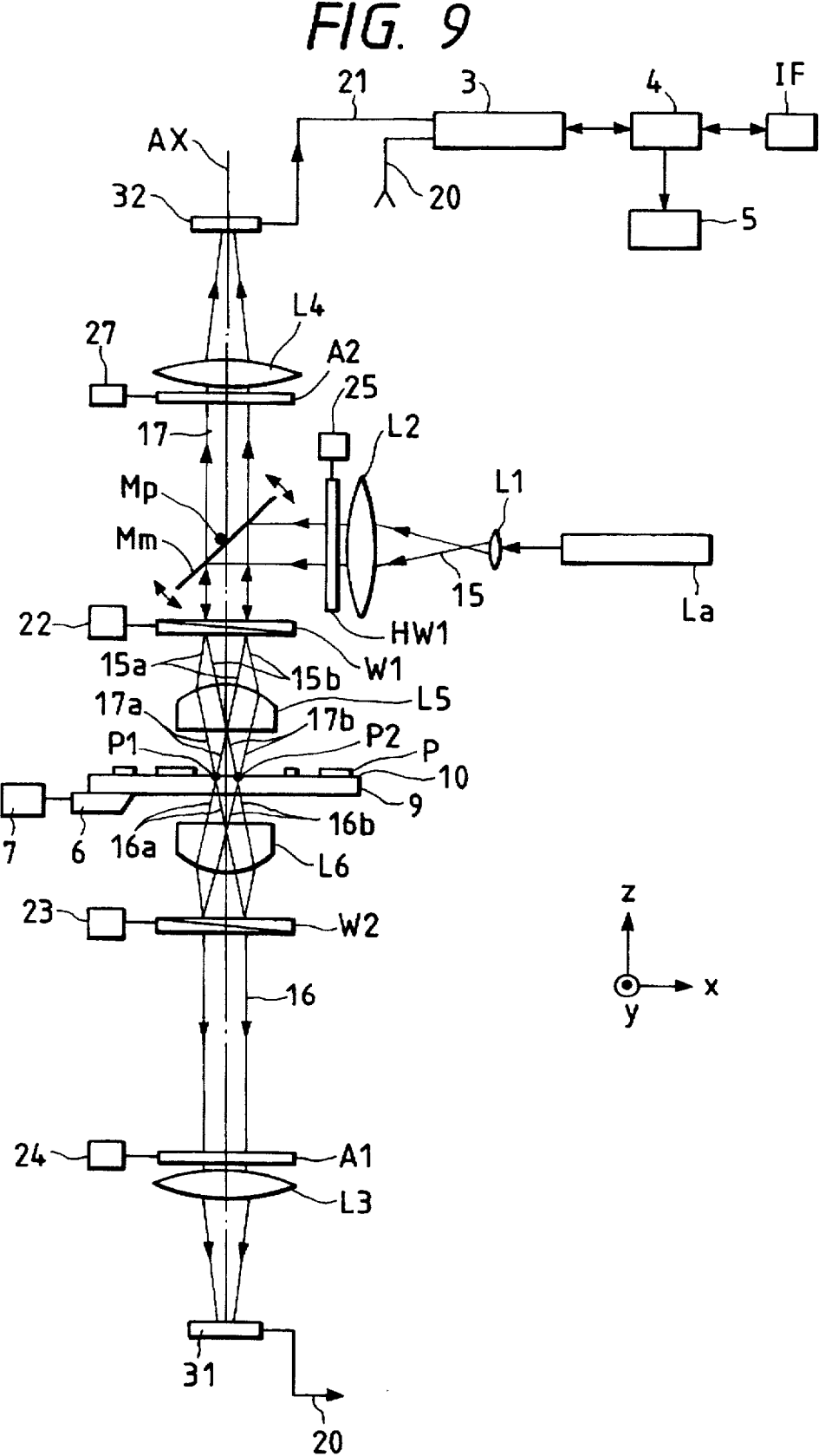
FIG. 9 is an explanatory view illustrating a third embodiment of the present invention.

FIG. 9 is an explanatory view showing a third embodiment of the present invention. A construction of the defect inspecting apparatus illustrated in FIG. 9 is substantially the same as that in FIG. 8. The same members are marked with the like symbols, and the detailed description thereof will be omitted. A different point between the apparatuses of FIGS. 8 and 9 is that photoelectric converting elements of the apparatus in FIG. 9 are silicon photo diodes and photo multipliers composed of single pixels and deviate from focal positions (where a pattern image of a mask R is formed) of lenses L3, L4, and a defocus image of the mask pattern is thus detected. Based on such a construction, unnecessary noises from the mask 9 can be prevented from striking on the photoelectric converting elements.

Further, in the apparatus of FIG. 9, the lenses L3, L4 may be omitted, and a photoelectric converting element 31 may be disposed in rear of the analyzer A1 (on the side opposite to the reticle 9) while a photoelectric converting element 32 may also be disposed in rear of the analyzer A2 (on the side opposite to the reticle 9). Referring to FIG. 9, the position behind the analyzer A1 is in a pupil position (such as position as to exhibit a relationship of Fourier transform with respect to the pattern of the reticle 9) of the lens L6 or has a relationship equal thereto. The position behind the analyzer A2 (on the side opposite to the reticle 9) is in a pupil position of the lens L5 or has a relationship equal thereto.

Figure 10:
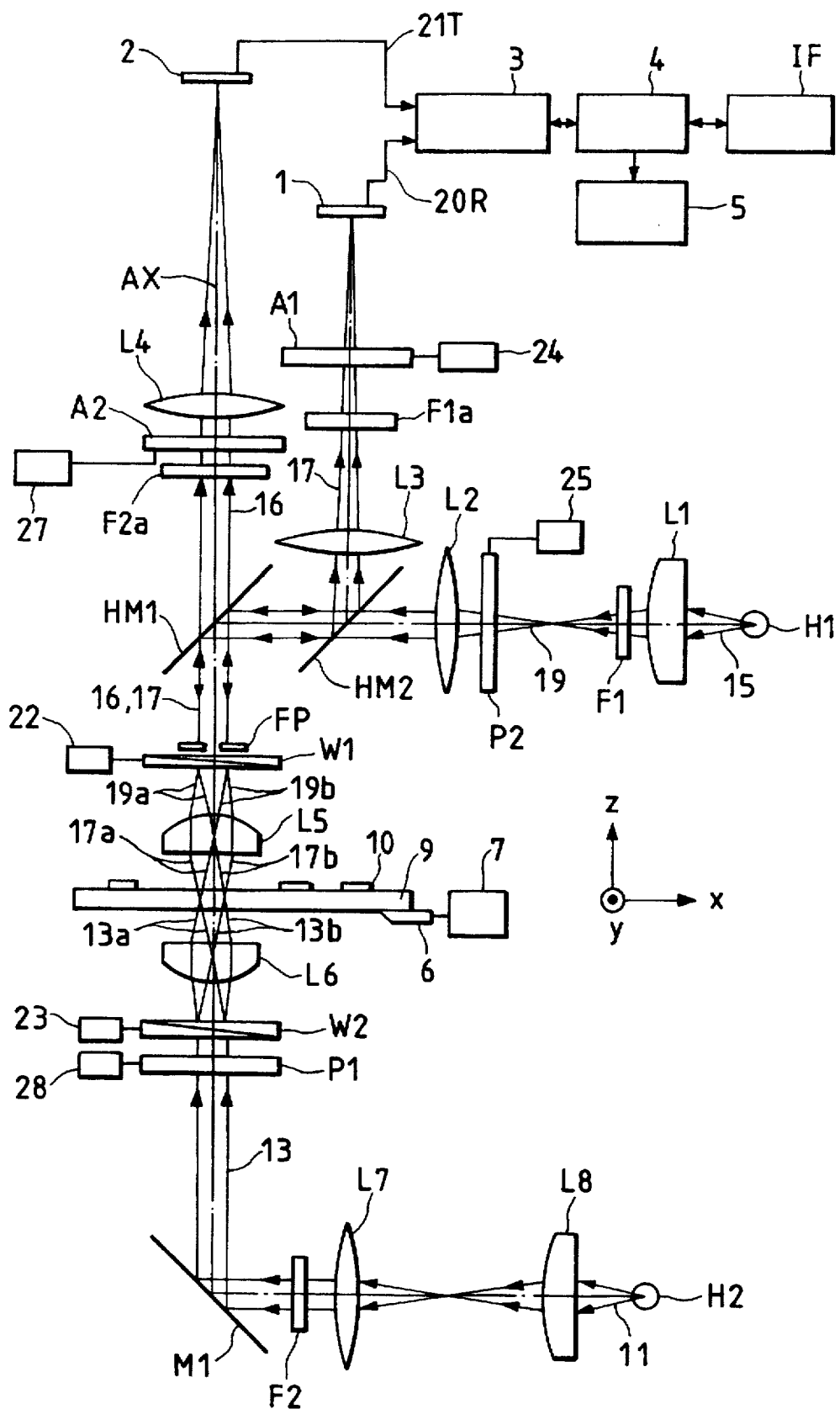
FIG. 10 is an explanatory view illustrating a fourth embodiment of the present invention.

FIG. 10 is an explanatory view illustrating a fourth embodiment of the present invention. In the apparatus shown in FIG. 10, the same members as those in FIG. 1 are marked with the like symbols, and the detailed description thereof will be omitted.

In accordance with the fourth embodiment, the R-DIC image is formed based on a wavelength band $\lambda_1$, while the T-DIC image is formed based on a wavelength band $\lambda_2$. Therefore, the light source of the apparatus illustrated in FIG. 1 is to be added. Further, filters F1, F2, F1a, F2a are also added, and the R-DIC image and the T-DIC image are formed with different wavelengths by use of the one objective lens L5. The filters F1, F1a transmit the wavelength band $\lambda_1$ but do not transmit the wavelength band $\lambda_2$. The filters F2, F2a transmit the wavelength band $\lambda_2$ but do not transmit the wavelength band $\lambda_1$. Filter characteristics are determined so that an overlap between the two wavelength bands passing through the filters F1a, F2a is reduced as much as possible. Light beams 19, 13 are rectilinear polarized light beams, and the polarization planes thereof make an angle of 45° to the directions of the wedges of the Wollaston prisms W1, W2. The analyzer A1 and the polarizer P1 are set in the cross Nicol relationship, and the analyzer A2 and the polarizer P2 are also set in the cross Nicol relationship. The light beams 15 emitted from the light source H1 penetrate the filter F1 and become light beams 19 having a wavelength $\lambda_1$. The light beams 19 travel through the polarizer P2, the lens L2 and the half-mirror HM2 and are reflected by the half-mirror HM1 along the optical axis AX. The light beams 19 then become two fluxes of rectilinear polarized light beams 19a, 19b orthogonal to each other. The reticle 9 is illuminated vertically with these light beams 19a, 19b. Light beams 17a, 17b including scattered beams generated pass through the Wollaston prism W1 and turn out the light beams 17. The light beams 17 travel through the half-mirrors HM1, HM2, penetrate a filter F1a and the analyzer A1 as well and are then incident on the two-dimensional photoelectric converting element 1, wherein the image is formed. The two-dimensional photoelectric converting element 1 outputs a signal 20R corresponding to a reflection image using the illumination light having the wavelength $\lambda_1$.

On the other hand, light beams 11 emitted from the light source H2 for transmission fall on the filter F2 via lenses L8, L7. The light beams from the light source H2 penetrate the filter F2 and become light beams 13 having a wavelength $\lambda_2$. The light beams 13 travel through the mirror M1 and the polarizer P1 and become rectilinear polarized light beams 13a, 13b orthogonal to each other through the Wollaston prism W2. These polarized light beams 13a, 13b penetrate the reticle 9 and are synthesized into light beams 16 after passing through the objective lens L5 and the Wollaston prism W1 as well. The light beams 16 pass through the half-mirror HM1, a filter F2a, the analyzer A2 and the lens L4 and are then incident on the two-dimensional photoelectric converting element 2, where the image is formed. The two-dimensional photoelectric converting element 2 outputs a signal 21T corresponding to a transmitting image illumination light having the wavelength $\lambda_2$.

In accordance with the fourth embodiment, it is desirable that the wavelength bands $\lambda_1$, $\lambda_2$ be set to wavelength bands as close as possible so that the resolution does not change in R-DIC, T-DIC. If impossible, a pupil restriction filter FP using a color filter is provided in the pupil of the objective lens L5 so that $\lambda_{10}/NA_R = \lambda_{20}/NA_T$ is established, where $\lambda_{10}$, $\lambda_{20}$ are the central wavelengths of $\lambda_1$, $\lambda_2$. This pupil restriction filter FP is a color filter which blocks the shorter wavelength but transmits the longer wavelength of the central wavelengths $\lambda_{10}$, $\lambda_{20}$.

Figure 11:
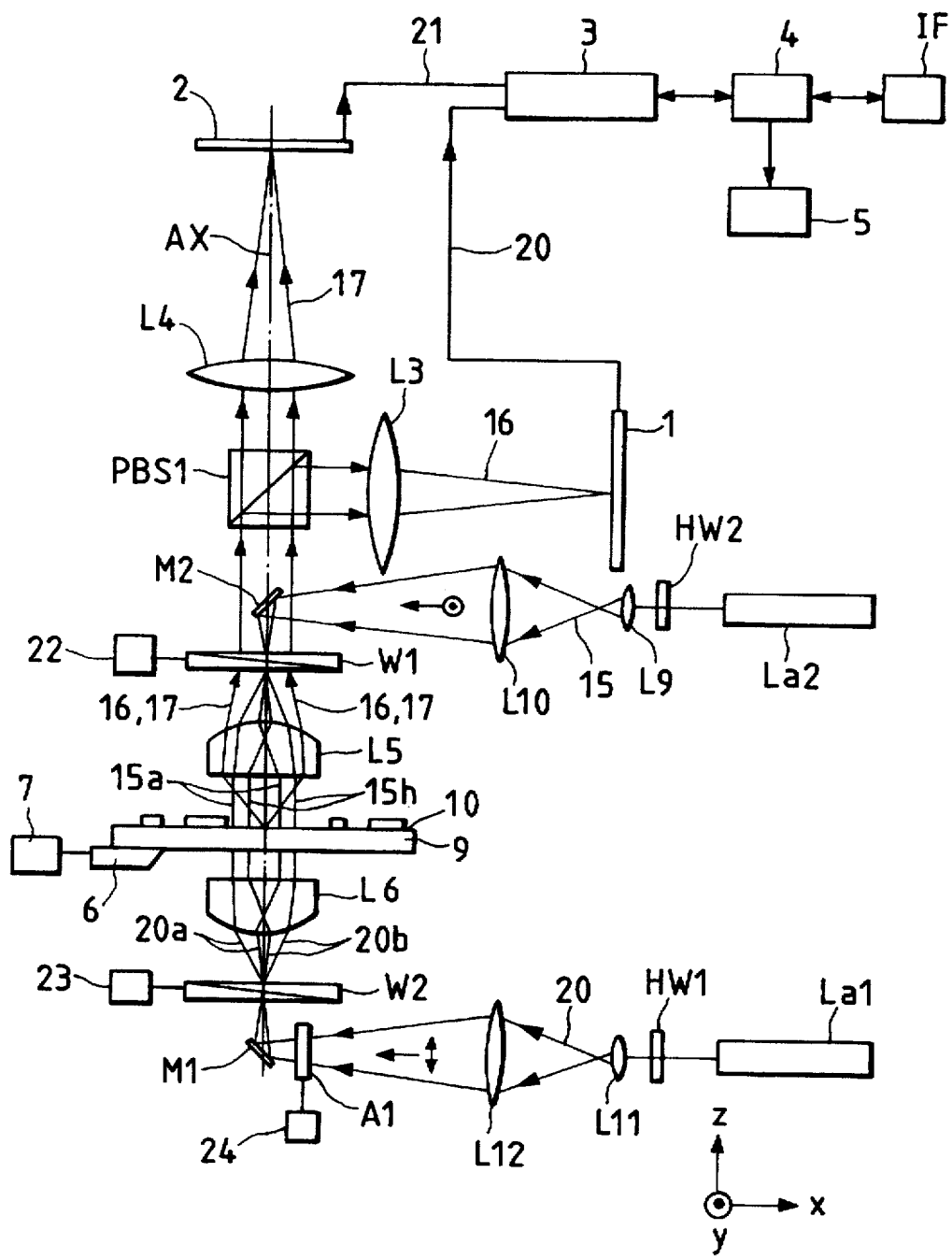
FIG. 11 is an explanatory view illustrating a fifth embodiment of the present invention.

FIG. 11 is a diagram illustrating a fifth embodiment of the present invention. The same members as those in FIG. 1 are marked with the like symbols. Lasers La1, La2 serving as light sources have the same wavelength. Light beams 15, 20 serve for the vertical illuminations and the transmitting illumination, respectively. The light beams are adjusted so that the polarization planes are directed at 45° to the directions of the two wedges of the Wollaston prisms W1, W2 by use of $\lambda/2$ plates HW1, HW2. Then, the light beams are also adjusted so that the light beams 15 take the polarization plane parallel to the sheet surface, while the light beams 20 take the polarization plane perpendicular to the sheet surface. The mirrors M1, M2 are small-sized reflecting mirrors and are located in the vicinity of the pupils of the objective lens L5 and a condenser lens L6 as well as performing a role of a spatial filter for blocking a 0-th order light beam. A position of the Wollaston prism W1 is adjusted by an adjuster 22 so that a phase difference between the light beams 15a, 15b is zeroed. A position of the Wollaston prism W2 is adjusted by an adjuster 23 so that there is zeroed a phase difference given when the light beams 19a, 19b (two fluxes of light beams polarizing directions of which are orthogonal) pass. A polarized beam splitter PBS1 transmits the polarized light beams having a polarization plane parallel to the sheet surface but reflects the polarized light beams having a polarization plane perpendicular thereto.

Under such setting, the laser La2 is switched ON, whereas the laser La1 is switched OFF. Hereupon, the R-DIC image turned out to be the optical dark field is obtained substantially as it is on the photoelectric converting element 2, while a Schliren method based image of the R-DIC image turned out to be optical bright field is obtained on the photoelectric converting element 1. Reversely when switching ON the laser La1 but OFF the laser La2, the T-DIC image turned out to be the optical dark field is obtained as it is on the photoelectric converting element 1, while the Schliren method based image of the T-DIC image turned out to be the optical bright field is obtained on the photoelectric converting element 2. If the two lasers are switched ON, the result is as follows:

Photoelectric Converting Element 1: A Dark Field T-DIC Image+B Bright Field R-DIC Image (Schliren Method)

Photoelectric Converting Element 2: C Dark Field R-DIC Image+D Bright Field T-DIC Image (Schliren Method)

Herein, for establishing A:B=C:D with respect to a light quantity ratio, the analyzer A1 controls a light quantity for the transmission illumination. If the object to be imaged is a circuit pattern, A and C are different only in their light quantities, and, B and D are also different only in their light quantities. The light quantity ratio has such a relationship as A/D=C/B, and, therefore, the analyzer A1 may be adjusted to establish A=C with respect to the intensity of the pattern image. Further, generally A/D≠C/B is established with respect to the intensity of the image of defect, and hence, even when trying to erase the pattern image by the imaging elements 1, 2, it remains unerased. Hence, the difference image may be processed in the same manner with the embodiments 1 to 4 discussed above.

According to the present invention, only the light transmitting defect can be detected by disappearing substantially the whole of the circuit pattern.

Further, the defect with a low contrast such as a phase object can be also detected.

It is apparent that, in this invention, a wide range of different working modes can be formed based on the invention without deviating from the spirit and scope of the invention. This invention is not restricted by its specific working modes except being limited by the appended claims.

What is claimed is:

1. A defect inspecting apparatus for detecting a defect on a mask formed with a predetermined pattern, comprising:

a first illumination system having a dividing optical element which divides light from a light source into first and second light beams for illuminating the mask with said first and second light beams for transmission through the mask;

a second illumination system having a dividing optical element which divides light from a light source into third and fourth light beams for illuminating the mask with said third and fourth light beams for reflection from the mask;

a first light receiving system having a first photoelectric converting element for receiving a differential interference image produced by said first and second light beams emitted from said first illumination system and transmitted through the mask;

a second light receiving system having a second photoelectric converting element for receiving a differential interference image produced by said third and fourth light beams emitted from said second illumination system and reflected by the mask; and a signal processing circuit for detecting a defect based on a signal from said first photoelectric converting element and a signal from said second photoelectric converting element.

2. The defect inspecting apparatus according to claim 1, wherein a wavelength of said first and second light beams is different from a wavelength of said third and fourth light beams.

3. The defect inspecting apparatus according to claim 1, wherein said light source of said first illumination system is common to said light source of said second illumination system.

4. The defect inspecting apparatus according to claim 1, wherein said signal processing circuit detects a defect based on a difference signal between the signal from said first photoelectric converting element and the signal from said second photoelectric converting element.

5. The defect inspecting apparatus according to claim 1, wherein said signal processing circuit detects a defect based on a relative signal between the signal from said first photoelectric converting element and the signal from said second photoelectric converting element.

6. The defect inspecting apparatus according to claim 1, wherein said first photoelectric converting element and said second photoelectric converting element are two-dimensional photoelectric converting elements.

7. A defect inspecting apparatus for detecting a defect on a mask formed with a predetermined pattern, comprising:
   a first illumination system for illuminating the mask with light beams for transmission through the mask;
   a second illumination system for illuminating the mask with light beams for reflection from the mask;
   a first light receiving optical system for receiving illumination light beams emitted from said first illumination system and transmitted through the mask and for forming an image;
   a second light receiving optical system for receiving illumination light beams emitted from said second illumination system and reflected by the mask and for forming an image;
   a first photoelectric converting element for detecting the image formed by said first light receiving optical system; and
   a second photoelectric converting element for detecting the image formed by said second light receiving optical system,
   wherein at least one of said first and second photoelectric converting elements is disposed at a position where a defocused image of said pattern is detected.

8. The defect inspecting apparatus according to claim 7, wherein said first and second photoelectric converting elements are photoelectric converting elements composed of single pixels.

9. The defect inspecting apparatus according to claim 8, wherein said photoelectric converting element composed of the single pixels is a silicon photo diode.

10. The defect inspecting apparatus according to claim 7, further comprising:
    a signal processing circuit for detecting a defect based on a signal from said first photoelectric converting element and a signal from said second photoelectric converting element.

11. The defect inspecting apparatus according to claim 10, wherein said signal processing circuit detects a defect based on a difference signal between the signal from said first photoelectric converting element and the signal from said second photoelectric converting element.

12. The defect inspecting apparatus according to claims 10, wherein said signal processing circuit detects a defect based on a relative signal between the signal from said first photoelectric converting element and the signal from said second photoelectric converting element.

13. A defect inspecting apparatus for optically detecting a defect on a mask formed with a predetermined pattern, comprising:
    an oscillation mirror;
    a first illumination system having a dividing optical element which divides light via said oscillation mirror from a light source into first and second light beams for illuminating the mask with said first and second light beams for transmission through the mask;
    a second illumination system having a dividing optical element which divides light via said oscillation mirror from a light source into third and fourth light beams for illuminating the mask with said third and fourth light beams for reflection from the mask;
    a first light receiving system having a first photoelectric converting element for receiving a differential interference image produced by said first and second light beams emitted from said first illumination system and transmitted through said mask; and
    a second light receiving system having a second photoelectric converting element for receiving a differential interference image produced by said third and fourth light beams emitted from said second illumination system and reflected by said mask.

14. The defect inspecting apparatus according to claim 13, wherein said light source of said first illumination system and said light source of said second illumination system are common lasers.

15. The defect inspecting apparatus according to claim 13, further comprising:
    a signal processing circuit for detecting a defect based on a signal from said first photoelectric converting element and a signal from said second photoelectric converting element.

16. The defect inspecting apparatus according to claim 15, wherein said signal processing circuit detects a defect based on a difference signal between the signal from said first photoelectric converting element and the signal from said second photoelectric converting element.

17. The defect inspecting apparatus according to claim 15, wherein said signal processing circuit detects a defect based on the basis of a relative signal between the signal from said first photoelectric converting element and the signal from said second photoelectric converting element.

18. The defect inspecting apparatus according to claim 13, wherein at least one of said first and second photoelectric converting elements is disposed at a position where a defocused image of said pattern is detected.

* * * * *